United States Patent
Martel

[11] 4,014,918
[45] Mar. 29, 1977

[54] PROCESS FOR THE PREPARATION OF CYCLOPROPANE DERIVATIVES AND COMPOUNDS PRODUCED THEREIN

[75] Inventor: Jacques Martel, Bondy, France

[73] Assignee: Roussel-UCLAF, Paris, France

[22] Filed: Sept. 23, 1975

[21] Appl. No.: 616,048

Related U.S. Application Data

[63] Continuation of Ser. No. 237,892, March 24, 1972, abandoned, which is a continuation of Ser. No. 841,132, July 11, 1969, abandoned.

[30] Foreign Application Priority Data

July 12, 1968 France .............................. 68.159066

[52] U.S. Cl. ......................... 260/468 H; 260/514 H
[51] Int. Cl.² ......................................... C07C 51/00
[58] Field of Search .................... 260/514 H, 468 H

[56] References Cited
OTHER PUBLICATIONS

House, Modern Synthetic Reactions, pp. 249–250, (1965).

Primary Examiner—Robert Gerstl
Attorney, Agent, or Firm—Hammond & Littell

[57] ABSTRACT

Process for the preparation of racemic or optically-active cyclopropane carboxylic acid of the formula

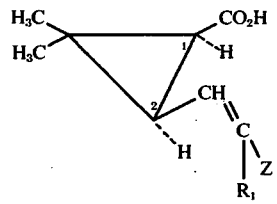

wherein the $CO_2H$ substituent on the carbon 1 and the

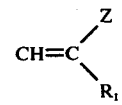

substituent on the carbon 2 are in the cis-position relative to one another, $R_1$ represents a hydrogen, an alkyl radical, an aralkyl radical, an aryl radical, an alkenyl radical, an alkynyl radical, a cycloalkyl radical, a cycloalkenyl radical, a heterocyclic radical, these radicals being able to be substituted, specifically by lower alkyl or lower alkoxy, or represents a cyano group, an acyl group, a formyl group, an alkoxycarbonyl group or a nitro group, and Z represents the $R_2$ residue which has the same meaning as $R_1$ but is identical or different thereto, or the $R_3$ residue, which represents an allyl radical, a benzyl radical, a cyano group, an acyl group, a formyl group, an alkoxycarbonyl group, or a nitro group, or $R_1$ and Z together form a saturated or unsaturated carbon homocycle or heterocycle, whose ring can support substituents such as lower alkyls or lower alkoxys, or functions such as ketonic functions, or together form a polycyclic aromatic residue such as a fluorene residue.

4 Claims, No Drawings

PROCESS FOR THE PREPARATION OF CYCLOPROPANE DERIVATIVES AND COMPOUNDS PRODUCED THEREIN

PRIOR APPLICATIONS

This application is a continuation of our copending, commonly assigned application Ser. No. 237,892 filed Mar. 24, 1972, now abandoned, which in turn is a continuation of our copending commonly assigned application Ser. No. 841,132 filed July 11, 1969, now abandoned.

OBJECTS OF THE INVENTION

It is an object of the invention to provide a process for the preparation of the compounds of formula I.

It is another object of the invention to provide novel compounds produced in the process of the invention.

These and other objects of the invention will become more apparent as the description of the invention proceeds.

DESCRIPTION OF THE INVENTION

The process for the preparation of the compounds of formula I, an object of the invention, is summarised on sheet I.

The process of the invention involves the preparation of racemic or optically-active cyclopropane carboxylic acids, of the formula

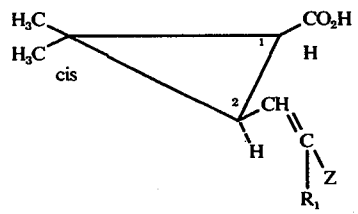

wherein R, represents a lower alkyl radical and such as an ester, II, of (1S,2S) configuration, with ozone in the presence of a lower alkanol, effects the reductive decomposition of the resultant oxidation compound by the action of a reducing agent and hydrolyses the resultant racemic or optically-active dialkylketal of the lower alkyl ester of the trans-3,3-dimethyl-2-formyl-cyclopropane-1-carboxylic acid, II', by the action of an acid reagent, in order to obtain the lower alkyl ester of the trans-3,3-dimethyl-2-formyl-cyclopropane-1-carboxylic acid of the formula

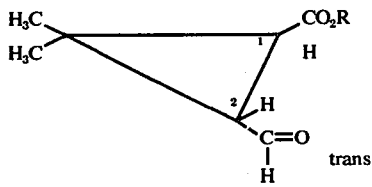

wherein R has the above-assigned meaning, submits the said ester to the action of a basic reagent, in order to obtain the lactone of the corresponding cis-3,3-dimethyl-2-(alkoxy-hydroxymethyl)-cyclopropane-1-carboxylic acid of the formula

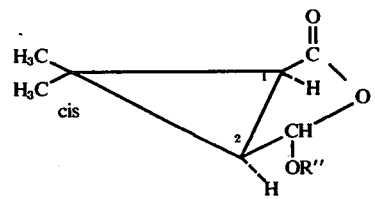

wherein R″ represents a lower alkyl radical, such as methyl, submits the said compound to the action of an aqueous medium, this medium being able to be slightly acidic or basic, in order to obtain the cis-3,3-dimethyl-2-formyl-cyclopropane-1-carboxylic acid, existing in the form of an internal hemi-acylal, of the formula

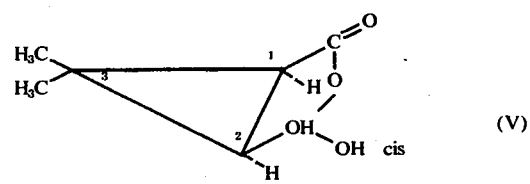

this compound being in racemic form, of (1S,2R) configuration or (1R,2S) configuration dependent upon whether the starting compound, II, is itself racemic, of (1S,2S) configuration or of (1R,2R) configuration, causes a phosphorous carbanionic reagent, which can exist in a basic medium in the form of an ylide of the formula

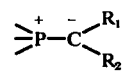

wherein $R_1$ and $R_2$ have the above-assigned meaning or in the form of a carbanion of the formula

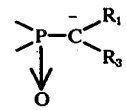

wherein $R_1$ and $R_3$ have the above-assigned meaning to react with the said compound V, and obtains the desired corresponding compound I, either in racemic form or with a configuration at 2 inverse to that or the starting compound II.

To avoid any possible confusion, it has been judged useful to define the compound from the process of this invention by the absolute configuration of their asymetric carbons at positions 1 and 2, according to the nomenclature of R. S. LAHN, Sir C. INGOLD and V. PRELOG /cf. experientia 12, 81 (1956); Angew. Chem. 78, 413 (1966)/.

So far as concerns the nomenclature, it is equally to be noted that the lactone, IV, of the cis-3,3-dimethyl-2-(alkoxy-hydroxymethyl)-cyclopropane-1-carboxylic acid can also be termed the lactone of the hemi-alkylketal of the cis-3,3-dimethyl-2-formyl-cyclopropane-1-carboxylic acid, and that the internal hemi-acylal of the cis-3,3-dimethyl-2-formyl-cyclopropane-1-carboxylic acid can also be designated as the lactone of cis-3,3-dimethyl-2-(dihydroxymethyl)-cyclopropane-1-carboxylic acid. Finally, the 3,3-dimethyl-2-(2′-methyl-1′- propenyl)-cyclopropane-1-carboxylic acid are designated as chrysanthemic acids and the 3,3-dimethyl-2-(2'-methoxycarbonyl-trans-1'-propenyl)-cyclopropane-1-carboxylic acids are called seq. trans-pyrethric acids.

According to the process of the invention, one can prepare compounds of formula I wherein $R_1$ equals $R_2$ equals alkyl such as ethyl, propyl, isopropyl, butyl, isobutyl, etc. . . . ; $R_1$ and $R_2$ equal aryl such as phenyl substituted or not; the compounds of formula I wherein $R_1$ and $R_2$ together represent a cycloalkyl radical such as cyclopropyl, cyclobutyl, cyclopentyl, cyclohexyl, substituted or not, or $R_1$ and $R_2$ together represent a heterocyclic radical such as pyranyl. Amongst the compounds I, prepared according to the process of the invention, one can quite specially cite the compounds I wherein $R_1$ equals $R_2$ equals $CH_3$, namely the cis-chrysanthemic acid $I_A$ and specifically the 1-cis-chrysanthemic (1S,2R) acid, convertable by epimerisation of the cetner 1 by processes known per se such as the process of M. JULIA et al., C. R. 248 242 (1959), into natural d-trans-chrysanthemic (1R,2R) acid, as well as the compounds I wherein $R_1$ equals $CH_3$ and $R_3$ equals —$CO_2$ Alkyl, and specifically the cis seq.trans-pyrethric acids, $I_B$, wherein $R_1$ equals $CH_3$ and $R_3$ equals $CO_2CH_3$, particularly the 1-cis acid of (1S,2R) configuration, this latter acid being convertable by epimerisation of the centre 1 -into natural d-trans seq. trans-pyrethric (1R,2R) acid, by application of the process described in copending, commonly assigned U.S. Pat. application Ser. No. 841,133 filed on even date herewith, the said process consisting essentially in preparing the 1-cis seq. trans-pyrethric (1S,2R) acid chloride, in epimerising the latter by heating, then in hydrolysing the epimerised (1R,2R) acid chloride (see sheet II).

It is in fact an object of the invention to disclose a process for the preparation of acids with cis-configuration, of formula I, of the chrysanthemic type such as $I_A$ or pyrethric type such as $I_B$, which by themselves can offer only a minimal biological interest, but which can easily be transformed, by various processes, into corresponding acids of trans-configuration such as the trans-chrysanthemic acid of the racemic series or more particularly of the d natural (1R,2R) series, and the trans seq.trans-pyrethric acids of the racemic series or more particularly of the d natural (1R,2R) series, which constitute the acid moiety of the natural or synthetic esters of the pyrethrinoid family, possessing remarkable insecticidal properties.

It is equally an important object of the present invention to disclose a process for the preparation of optically-active acids $I_A$ and $I_B$, of (1S,2R) configuration, which makes it possible to employ as starting materials the lower alkyl esters of 1-trans-chrysanthemic acid, II, of (1S,2S) configuration. These esters are obtained specifically by esterification of the 1-trans-chrysanthemic (1S,2S) acid. This latter acid, an antipodal compound of natural chrysanthemic acid and whose pyrethrinoid esters display an insecticidal activity much inferior to that of the natural d-trans acid esters, is obtained during the resolution of dl-trans-chrysanthemic acid, itself prepared according to the process described in U.S. Pat. No. 3,445,499.

The process of the present invention therefore in particular makes it possible to restore value to 1-trans-chrysanthemic (1S,2S) acid which, up till now, constituted a useless by-product of the chrysanthemic synthesis.

This restoration of value requires the following stages: resolution of the dl-trans-chrysanthemic acid, isolation of the d-trans (1R,2R) and 1-trans (1S,2S) acids, conversion of the 1-trans-chrysanthemic acid into the corresponding (1S,2S) ester, conversion of this trans (1S,2S) ester in accordance with the present invention into acids such as $I_A$ or $I_B$ of cis (1S,2R) configuration, conversion of these acids into natural chrysanthemic or pyrethric acids of (1R,2R) configuration, either so far as concerns the chrysanthemic series by known processes, such as that described by M. JULIA C. R. 248, 242 (1959), or so far as concerns the pyrethric series by the process described in copending, commonly assigned United States patent application Serial Number., filed on even date herewith.

It goes without saying, however, that the process of the present invention can be applied generally. It is not limited to starting only from the (1S,2S) series derived from 1-trans-chrysanthemic acid, the disclosed reactions can equally be put to use in the (1R,2R) series or the racemic series, derived respectively from the d-trans and from the dl-trans-chrysanthemic acid. The starting product can equally be a mixture of racemic and optically active compounds, of trans-configuration or even of trans and cis configuration, such as a mixture of dl-cis and trans-chrysanthemic acid esters. In the latter case, the compounds $I_A$ and $I_B$ obtained according to the process of the invention are then constituted by the cis racemic forms.

The process of the preparation of the compounds I, starting from the compounds II, includes according to the present invention four successive stages of which two are particularly characteristic.

It relates to the transformation of the compound III, of trans structure, into the compound IV of cis structure, by inversion of the configuration at the centre 2 and maintenance of that at the center 1, and to the transformation of the compound into the compound I, while retaining the configurations at the centres 1 and 2.

The problem of replacing the unsaturated chain in the chrysanthemic series by an aldehydic grouping had never been satisfactorily solved up till now, so far as one knows.

Progressive oxidation, in two steps, employing two oxidising reagents acting in succession, leads to the formation of a diol or ketol grouping, then to the aldehyde function /cf. M. MATSUI and H. YOSHICKA Agr. Biol, Chem. Jap. Vol 28 No. 1, page 32 (1964)/ or the oxidation then the controlled reduction of the resultant compound, while respecting the aldehydic grouping formed /cf. S. H. HARPER and H.W.B. REED J. Sci. Food, Agr. 2, 414 (1951)/seems in fact to provide only slightly increased yields and to be capable of operation only with difficulty on an industrial scale.

At present, this delicate problem has been resolved by carrying out the ozonolysis of a lower alkyl ester of the trans-chrysanthemic acid in the presence of a lower alkanol such as methanol, at low temperature, then by effecting the reductive decomposition of the oxidation compound formed, by means of a dialkyl sulphide. The employment of ozone in a methanolic medium with the reduction by a dialkyl sulphide, this latter method being incidentally known so far as concerns the action of dimethyl sulphide /cf. JAMES J. PAPPAS et al. Tetra. Letters, 36, 4273 (1966)/has made it possible to obtain the lower alkyl esters of the trans-3,3-dimethyl-2-formyl-cyclopropane-1-carboxylic acids, with a greatly increased yield of the order of 90% in the case of the methyl ester, starting from the corresponding lower alkyl esters of the corresponding d, l or racemic trans-chrysanthemic acids.

This stage of the process of the invention can be characterised by the points set out below.

The ozonolysis is effected by bubbling in of a mixture of oxygen and ozone, at low temperature. The temperature of the order if −75° C to −80° C seems to suit particularly well. The solvents which one preferably employs to effect this ozonolysis are the lower alkanols and specifically methanol; one can equally employ an organic solent such as ethyl acetate, chloroform, carbontetrachloride, etc. . . . , in admixture with a lower alkanol.

The reduction of the oxidation compound formed by the action of the ozone can be effected by different methods. One can specifically utilize powdered zinc in an aqueous medium as the reducing agent, by analogy with the technique of M. JULIA et al. /Bull. Soc. Chim. (1965) 1007/, concerning the ozonolysis of the pyrethric acid, one can specifically employ sodium sulphite or bisulphite, potassium ferrocyanide, a trialkyl phosphite, specifically trimethyl phosphite /cf. W.S. KNOWLES and Q.E. THOMPSON J. Org. Chem., 25, 1031 (1960), or equally hydrogen in the presence of a suitable catalyst such as palladized calcium carbonate containing 5% of palladium, according to the process of S. H. HARPER and H. W. REED /J. Sci. Food Agr. 2, 414 (1951)/. However, the method of application of the invention actually preferred consists in employing a dialkyl sulphide, specifically dimethyl sulphide, to effect this reductive decomposition. The reduction is then advantageously effected at a temperature of the order of −40° C; it leads, above all in the case when the ozonolysis has been effected in an alcoholic medium, to the obtaining of a product constituted by the dialkyl-ketal of a lower alkyl ester of a racemic or optically-active trans-3,3-dimethyl-2-formyl-cyclopropane-1-carboxylic acid, II′, which contains generally a certain quantity of the lower alkyl ester of the trans-3,3-dimethyl-2-formyl-cyclopropane-1-carboxylic acid, III, formed by partial hydrolysis of II′. It is necessary to complete this hydrolysis by the action of an acid agent such as acetic acid, which thus makes it possible to obtain the lower alkyl esters of racemic or optically-active trans-3,3-dimethyl-2-formyl-cyclopropane-1-carboxylic acids. All these reactions, in the course of which compounds with free aldehydic functions are formed, are carried out under an inert atmosphere to avoid any possible oxidation to the greatest extent.

The conversion of a compound of the type III thus obtained, of trans structure, into an epimeric compound of cis structure, without racemisation in the case when one is operating in an optically-active series, moreover does not seem in principle an easy operation to perform. One knows in fact that in the chrysanthemic series, the compounds of trans configuration are thermodynamically more stable then the corresponding compounds of cis configuration, and that it is therefore the cis → trans conversion which is favoured at the expense of the reverse conversion. Furthermore, a tendency towards epimerisation of the asymetric centre 2 of the compound III, making use of the activation induced by the aldehydic carbonyl, could equally lead to a temporary modification of the structure of the asymetric carbon 1, which carries an enolisable ester group, and consequently could tend to the racemisation of the optically-active compound III.

However, it has now been found that it is possible to achieve the desired result by treating the compound III by basic reagent. This treatment has the effect, probably via the aldehydic enolate, of promoting the inversion of center 2, which leads to a compound of cis configuration which can stablise itself by forming on internal hemi-acylal of type IV. To attain this unexpected result one preferably employs, as the basic reagent, and alcoholate / corresponding alcohol couple, and one operates in a non-aqueous medium.

In a particular preferred method of operation, one employs an alkali metal methylate / methanol couple, specifically the sodium methylate / methanol couple. Under these conditions, it seems indeed that the product formed, namely the etherified hemi-acylal (IV, with $R'' = -CH_3$), is accompanied by a certain quantity of free hemi-acylal, V.

This compound V is obtained in the following stage, by treating the compound IV with a hydrolysing medium; this hydrolysis is effected under relatively weak conditions in order not to disturb the cis structure. For this purpose, one can employ merely water or a neutral aqueous medium formed by a mixture of water and another solvent such as an alcohol like methanol or ethanol, a cyclic ether oxyde or an amide like dimethylformamide.

One can equally operate in a slightly acidic aqueous medium, for example in a water / acetic acid medium or in a dilute hydrochloric medium or in a slightly basic aqueous medium, utilising for example a dilute aqueous solution of sodium bicarbonate.

It does however seem well to advise against any medium too strongly alkaline such as aqueous soda lye.

An actually preferred method of operation consists in employing a water / dioxan medium or a water / carbonic acid gas medium for this hydrolysis.

The last stage of the process of the invention (summerised specifically for obtaining 1-cis-chrysanthemic acid and 1-cis seq. trans-pyrethric acid on sheet IV) is equally remarkable. It was in fact necessary to reconstruct the unsaturated chain of compounds such as $I_A$ or $I_B$, starting from compound V of cis structure, without causing any inversion of the configuration at centre 2, specifically one which would have had the effect of leading to the undesired formation of a compound of trans structure, and therefore without modification of the stereochemistry of the product originally subjected to treatment.

It has been found that it is possible to secure the compound I of the desired cis, by treating the hemi-acylal, V, by a phosphorus carbanionic reagent which is able to exist in a basic medium in the form of an ylide of type VIa, or in the form of a carbanion of type VIb.

Amongst these reagents one can cite the triaryl-alkyl phosphonium salts, specifically the triphenyl-alkyl phosphonium salts, which under the effect of a strong base give rise to an alkylidene phospherane of type VIa, the (tris-dialkylamino)-alkyl phosphonium salt, the /(bis-dialkylamino)-aryl/-alkyl phosphonium salt and the (dialkylamino-diaryl)-alkyl phosphonium salt which, under the action of a strong base, similarly give rise to an ylide of type VIa, as well as activated derivatives of oxygenated phosphorus compounds, such as oxides of phosphine, phosphinic esters and phosphonic esters which, in the presence of a strong basic agent, react in the form of a carbanion of type VIb.

To carry out the process of the invention, it seems to be preferable to employ a triphenyl-alkyl phosphonium salt or a phosphonic ester.

The reaction is effected under the usual conditions of the Wittig reaction and associated reactions, specifically employing as the basic agent which generates the desired ylide or carbanion on alkali metal hydride, an alkali metal amide, an organo-lithium compound or an alkali metal alcoholate, and as the solvent an ether such as diethyl ether, tetrahydrofuran or dimethoxyethane, an amide such as dimethylformamide, an alcohol in the presence of its alkali metal alcoholate or a hydrocarbon such as benzene or cyclohexane.

Thus it is that one prepares the racemic or optically-active cis seq. trans-pyrethric acids, by condensation of 0,0-diethyl 1-methoxy-carbonyl-ethyl phosphonate with the corresponding lactones of racemic or optically active cis-3,3-dimethyl-2-dihydroxymethyl-cyclopropane-1-carboxylic acids in the presence of sodium amide or sodium methylate, or one prepares the racemic or optically-active cis-chrysanthemic acids by condensation of triphenyl-isoproply phosphonium iodide with the same corresponding lactones in the presence of sodium hydride.

The compounds thus obtained may contain a slight quantity of undesirable opimers. These epimers are then separated by the standard methods employed in similar cases, specifically by combination with suitably chosen optically-active bases or by fractional distillation. Certain details concerning these separations are given subsequently in the experimental section.

The esters of racemic trans-chrysanthemic acid employed at the outset of the invention, can be prepared starting from dl-trans-chrysanthemic acid, according to known processes, specifically by employing the process described in U.S. Pat. No. 3,445,499.

The esters of the d-trans (1R,2R) series can be prepared according to known processes by esterification of the natural d-trans-chrysanthemic acid, itself derived from the hydrolysis of natural pyrethrins or from resolution of dl-trans-chrysanthemic acid, obtained by a synthetic route; this resolution can specifically be effected according to the process described by CALT- BELL /J. Sci. Food, 3 (1952) 189/ or according to the process described in copending, commonly assigned U.S. Pat. application Ser. No. 742,485, filed July 5, 1968, a process which is based on the selective insolubilisation of the D (—) thero-1-p-nitrophenyl-2-dimethylaminopropane-1,3-diol salt of d-trans-chrysanthemic (1R,2R) acid in a solvent or a suitable mixture of solvents such as methanolic isopropyl ether containing 15% of methanol.

As for the esters of the 1-trans (1S,2S) series, they can be obtained, according to known processes, by esterification of 1-trans-chrysanthemic acid derived equally by resolution of dl-trans-chrysanthemic acid by selective insolubilisation of its L (+) threo-1-p-nitrophenyl-2-dimethylaminopropane-1,3-diol salt. Thus it is that the methyl esters of the d, 1 or racemic trans-chrysanthemic acids can be prepared by the action of diazomethane on the corresponding acid or by esterification of the corresponding acid chloride by methanol in the presence of pyridine.

The terbutyl esters of the d, 1 or racemic trans-chrysanthemic acids can be obtained by transesterification by making an alkali metal terbutylate react upon the methyl esters of the corresponding trans-chrysanthemic acids.

A variant of the process of the invention, summarised on sheet III, has as its object a process for the preparation of racemic or optically-active cis-3,3-dimethyl-2-formyl-cyclopropane-1-carboxylic acids, existing in the form of the internal hemi-acylal of the formula:

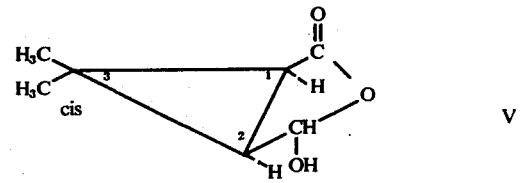

starting from racemic or optically-active trans-chrysanthemic acids or from their lower alkyl esters, with a configuration at position 2 inverse to that of the compounds V.

This variant of the process of the invention is characterised in that one treats a racemic or optically-active trans-3,3-dimethyl-2-(2'-methyl-1'-propenyl)-cyclopropane-1-carboxylic acid (or trans-chrysanthemic acid), or a lower alkyl ester thereof of the formula:

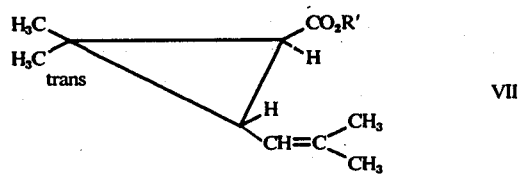

wherein R' represents hydrogen or a lower alkyl radical, with ozone, in the presence of a lower alkanol, effects reductive decomposition of the resultant oxidation compound by the action of a reducing agent, and hydrolyses the resultant racemic or optically-active dialkyl ketal of the formula:

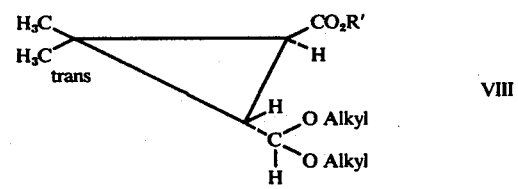

wherein R' has the above assigned meaning and the alkyl substituent represents a lower alkyl radical, by the action of an acid agent, so as to obtain the corresponding 2-formyl derivative which one saponifies, when R' represents a lower alkyl radical, by the action of a basic agent under an inert atmosphere, causes the racemic or optically-active 2-formyl derivative obtained, of the formula:

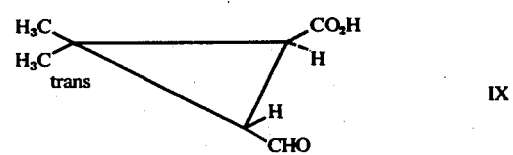

to react with a lower alkanol, submits the resultant dialkyl-ketal of the trans-3,3-dimethyl-2-formyl-cyclopropane-1-carboxylic acid, of the same configuration at 1 and 2 as the corresponding starting compound, and having the formula:

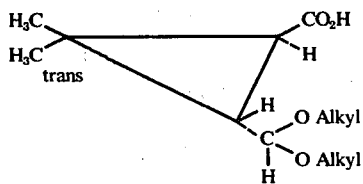

wherein the alkyl substituent has the above assigned meaning, to the action of an acid agent, so as to obtain the lactone of the hemi-alkyl-ketal of the racemic or optically-active cl-3,3-dimethyl-2-formyl-cyclopropane-1-carboxylic acid of the formula:

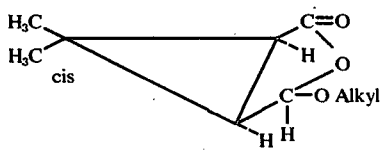

wherein the alkyl substituent has the previously indicated meaning, submits the said compound to the action of an aqueous medium, this medium being able to be slightly acidic or basic, and isolates the desired internal hemi-acylal of the racemic or optically-active cis-3,3-dimethyl-2-formyl-cyclopropane-1-carboxylic acid.

The variant of the process of the invention includes a particularly characteristic transformation. This concerns the conversion of the compound X of trans configuration into the compound IV of cis configuration, then into the compound V of cis configuration.

It is in fact surprising that the dialkyl-ketal of an optically-active trans-3,3-dimethyl-2-formyl-cyclopropane-1-carboxylic acid, submitted to the action of an acid agent, with elimination of the alkanol formed, leads to the lactone of the hemi-alkyl-ketal of the optically-active cis-3,3-dimethyl-2-formyl-cyclopropane-1-carboxylic acid, with a configuration at 2 inverse to that of the corresponding diketal, then by hydrolysis with maintenance of the configuration, to the corresponding optically-active cis-3,3-dimethyl-2-formyl-cyclopropane-1carboxylic acid, existing in the form of the cyclic hemi-acylal, V.

The variant of the process of the invention can be characterised by the following points:

The ozonolysis and the reduction of the oxidation compound formed can be effected according to the methods indicated above by the process of the invention. It is to be noted that, in order to eliminate the non-carbonylated impurities, one can after elimination of the solvent carry out a treatment with Reagent T (trimethyl-amino-aceto-hydraside) in acidic medium.

The acid agent, by means of which one effects the hydrolysis of the dialkyl-ketal of the racemic or optically-active trans-3,3-dimethyl-2-formyl-cyclopropane-1-carboxylic acid, or of a lower alkyl ester thereof, is acetic acid.

The saponification of the lower alkyl ester of the trans-3,3-dimethyl-2-formyl-cyclopropane-1-carboxylic acid, VIII' (R' = lower alkyl), is conveniently effected by the action of an alkaline agent such as an alkali metal hydroxide like sodium or potassium hydroxide. This saponification can be effected in the presence of an organic solvent such as an alkanol. The saponification and the treatments which follow it must be effected under an inert atmosphere in order to avoid so far as possible any oxidation of the aldehydic function.

The lower alkanol which one condenses with the trans-3,3-dimethyl-2-formyl-cyclopropane-1-carboxylic acid, IX, in order to obtain the dialkyl-ketal, X, is specifically methanol or ethanol.

The elimination of the water during this condensation is conveniently secured by distillation of the reaction mixture and recycling of the distillate over a dehydration agent such as magnesium or sodium sulphate, so-called "silliporite" (dehydrated alkali metal aluminium silicate), so-called "silicagel" (dehydrated silica gel) or so-called "drierite" (anhydrous calcium sulphate). During the condensation of IX with the alkanol, one can equally achieve elimination of the water by continuous distillation and simultaneous addition of alkanol, in such a manner as to maintain the volume of the reaction mixture constant. This latter method is not applicable with methanol, which does not form an azeotropic mixture with water.

The acid agent which one causes to act on the dialkyl-ketal of the trans-3,3-dimethyl-2-formyl-cyclopropane-1-carboxylic acid, X, in order to obtain the lactone IV, is specifically para-toluene-sulphonic acid or benzene-sulphonic acid.

The elimination of the alkanol formed by the action of the acid agent on the dialkyl-ketal of the trans-3,3-dimethyl-2-formyl-cyclopropane-1-carboxylic acid, X, is secured by distillation, with or without the simultaneous addition of a third solvent which forms with the alkanol an azeotropic mixture.

The hydrolysis of the lactone of the hemi-alkyl-ketal of the cis-3,3-dimethyl-2-formyl-cyclopropane-1-carboxylic acid, IV, is conveniently brought about by heating of this lactone, in an aqueous medium, possibly in the presence of a third solvent such as an alkanol like methanol or ethanol, a cyclic ether or an amide like dimethylformamide. One can equally operate in a slightly acidic aqueous medium, for example in a water / acetic acid medium or in a slightly basic aqueous medium employing for example a dilute aqueous solution of sodium bicarbonate.

It seems however well to advise against too strongly alkaline a medium, such as aqueous soda lye. This hydrolysis takes place advantageously in a water / dioxan medium or a water / carbonic acid gas medium, at ambient temperature.

Sheet I
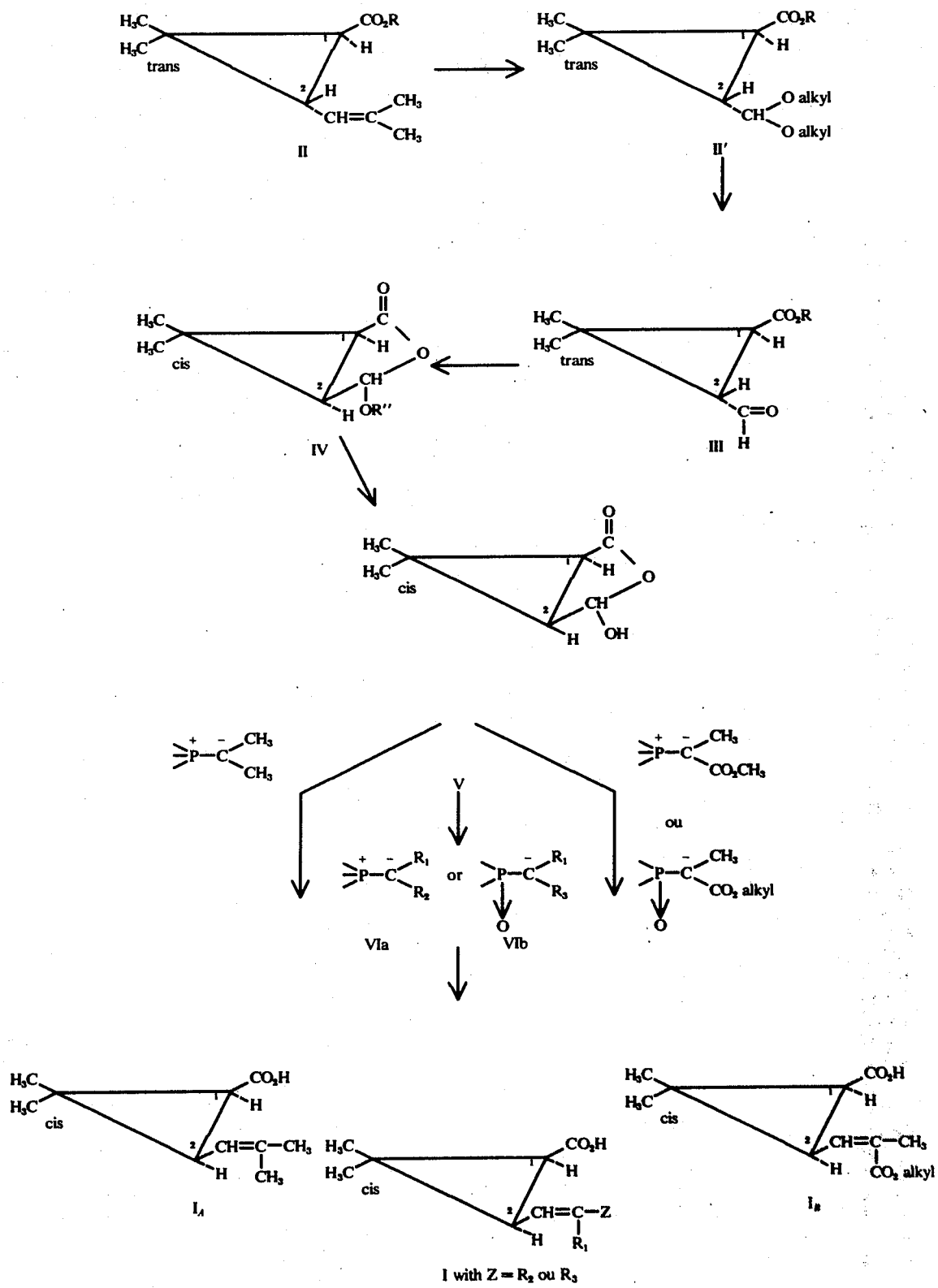

Sheet II
-continued
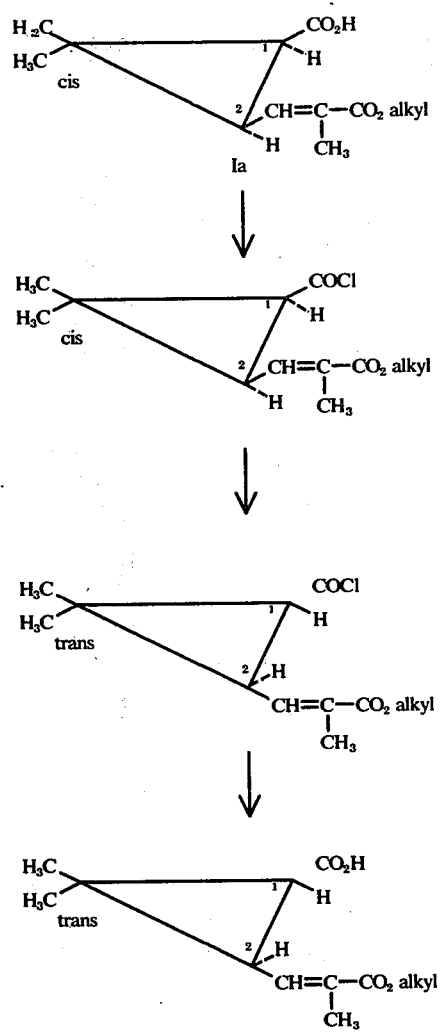
Sheet III
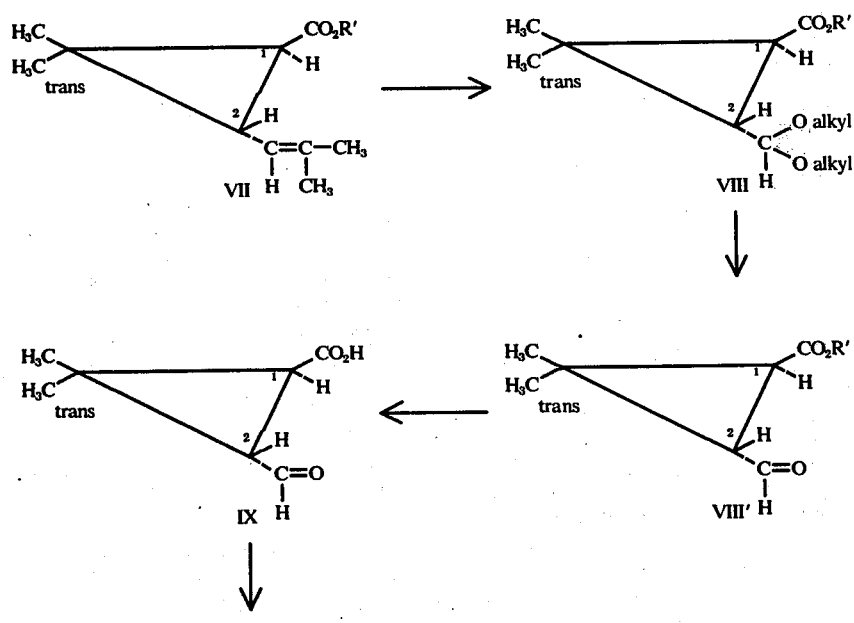

-continued

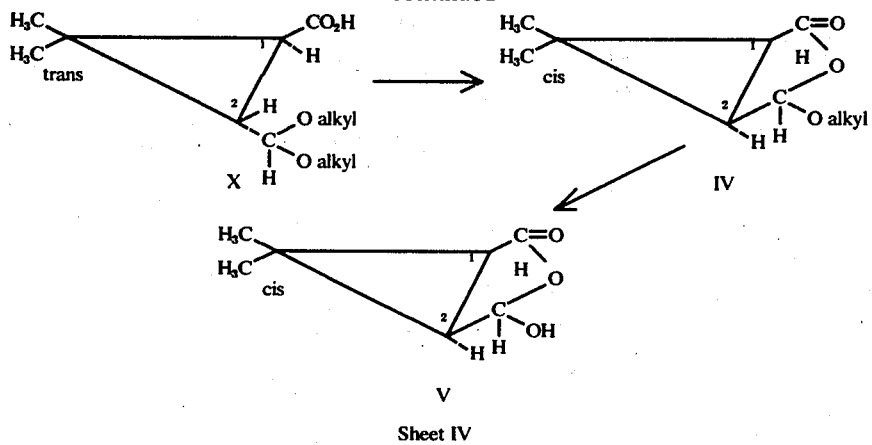

Sheet IV

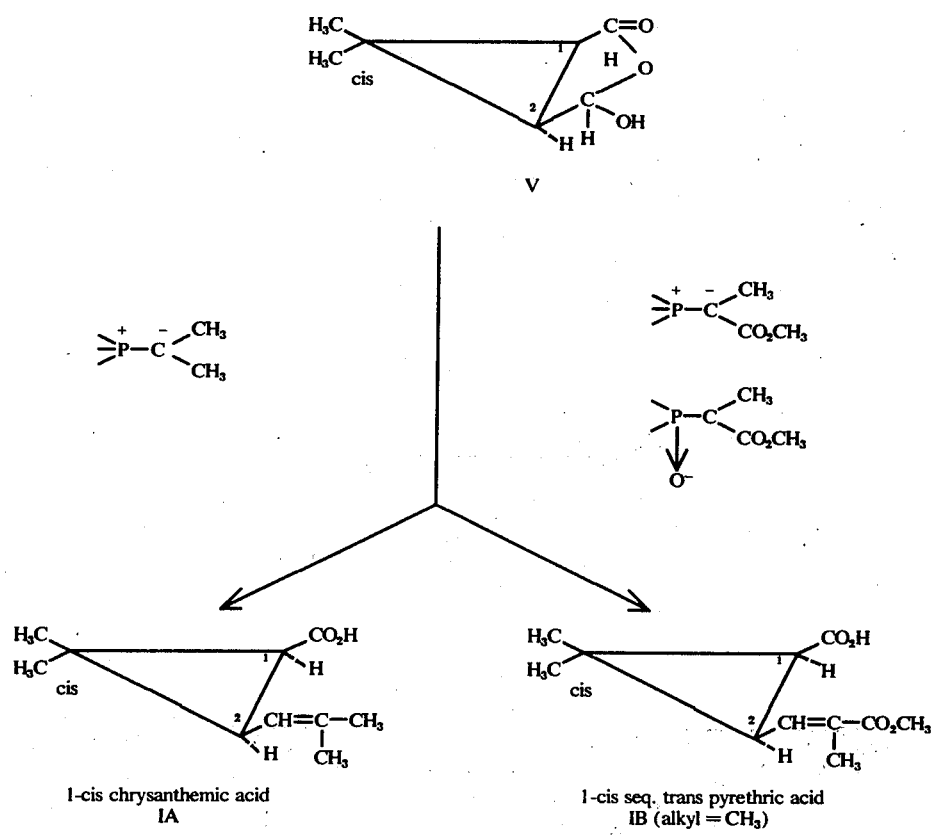

The following Examples illustrate the invention without limiting it in any way.

Preparations:

Preparation I : Methyl ester of 1-trans-chrysanthemic (1S,2S) acid /(II) with R = -CH₃/—

Stage A: 1-trans-chrysanthemic (1S,2S) acid chloride

Into 140 cc of petroleum ether (b.pt. = 35°—70° C), one introduces 73.5 g of 1-trans-chrysanthemic (1S,2S) acid (see Note) then, drop by drop over several minutes, 35 cc of thionyl chloride, agitates for two hours at ambient temperature, eliminates the volatile fractions by distillation under reduced pressure, then redistills under a more powerful vacuum, and obtains 80 g of 1-trans-chrysanthemic (1S,2S) acid chloride, b.pt. -65° C under 0.4 mm of mercury.

Note: The 1-trans-chrysanthemic (1S,2S) acid is obtained specifically by resolution of the racemic acid, for example by the intermediary of its D (+)-threo 1-p-nitrophenyl 2-dimethylamino-propane 1,3-diol salt, according to the process described in the above mentioned patent application Ser. No. 742,485.

Stage B: Methyl ester of 1-trans-chrysanthemic (1S,2S) acid

Into a mixture of 80 cc of petroleum ether (b.pt. = 35°–70° C) and 80 g of 1-trans-chrysanthemic (1S,2S) acid chloride, one introduces, drop by drop while cooling, a mixture of 55 cc of methanol and 65 cc of pyridine, agitates for forty-eight hours, separates the organic phase by decantation, washes it successively with an aqueous solution of hydrochloric acid, with water, with an aqueous solution of sodium bicarbonate, with water, dries it, concentrates it to dryness under reduced pressure, then redistills it under a good vacuum, and obtains 75.6 g of the methyl ester of 1-trans-chrysanthemic (1S,2S) acid, b.pt. = 56° C under 0.15 mm of mercury,$[\alpha]_D^{20} = -19°$ ($c = 1.4\%$ ethanol).

In an analogous manner, starting from d-trans-chrysanthemic (1R,2R) acid or from racemic trans-chrysanthemic acid, one obtains respectively the methyl ester of d-trans-chrysanthemic (1R,2R) acid or the methyl ester of racemic trans-chrysanthemic acid.

By esterification of the dl, d or l-trans-chrysanthemic acid chlorides with lower alcohols other than methanol, one obtains in an analogous fashion various lower alkyl esters of dl, d or l-trans-chrysanthemic acids.

The d-trans-chrysanthemic acid is obtained according to the process described in the above mentioned patent application Ser. No. 742,485.

Preparation II: Ter. butyl ester of dl-trans-chrysanthemic acid

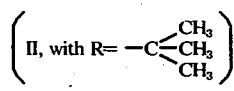

Into 300 cc of toluene, one introduces, under an atmosphere of nitrogen, 38 g of potassium terbutylate and 26.6 g of methyl dl-trans-chrysanthemate, agitates for one hour and fifteen minutes, introduces without exceeding +35° C, 200 cc of an aqueous 2 N solution of hydrochloric acid, separates the organic phase by decantation, then, after extraction with ether and elimination of the solvents by distillation under reduced pressure, obtains 29.35 g of crude terbutyl-dl-trans-chrysanthemate containing a little methyl ester. In order to eliminate the methyl ester, one adds to 29.35 g of the crude product 50 cc of methanol, 20 cc of water and 150 cc of a methanolic 2 N solution of soda. This is taken to reflux for one hour, the methanol is eliminated by distillation under reduced pressure, then by extraction with ether one obtains, after elimination of the solvents and redistillation, 21 g of the terbutyl ester of the dl-trans-chrysanthemic acid, b.pt. = 112° C under 15 mm of mercury, $n_D^{26} = 1.4530$.

In an analogous manner, one prepares the other lower alkyl esters of racemic or optically active trans-chrysanthemic acid, by transesterification, starting from the corresponding methyl ester. This method is particularly suitable for secondary or tertiary alcohols.

EXAMPLE I:

Cis-3,3-dimethyl 2-(2'-methoxycarbonyl-trans-1'-propenyl) (Sheet I) cyclopropane-1-carboxylic (1S,2R) acid or 1-cis seq. trans-pyrethic (1S,2R) acid ($I_B$) of cis (1S,2R) configuration or (I) with $R_2 = -CH_3$, $Z = CO_2CH_3$ and cis (1S,2R) configuration Stage A: Dimethyl-ketal of the methyl ester of trans-3,3-dimethyl 2-formyl cyclopropane-1-carboxylic (1S2S) acid (II') with $R = -CH_3$ alkyl $= -CH_3$ and trans (1S,2S) configuration.

Treatment with ozone

One passes a current of ozone into a solution, cooled to −80° C, of 70 g of the methyl ester of 1-trans-chrysanthemic (1S,2S) acid in 700 cc of methanol, for about three and a half hours, then drives off the excess ozone by a current of argon, while always maintaining the temperature at −80° C.

Reduction by dimethyl-thioether:

The methanolic solution obtained above is carried to −40° C and one adds to it, while agitating, 79 cc of dimethyl-thioether. One allows the temperature to raise itself to about 20° C and keeps the reaction mixture under agitation and nitrogen for some hours. One eliminates the methanol by distillation under reduced pressure, takes up the residue in methylene chloride, washes with an aqueous solution of sodium bicarbonate then with water, dries and concentrates to dryness under reduced pressure.

In this way one obtains 75.9 g of an oil which contains the methyl ester of the dimethyl-ketal of the trans-3,3-dimethyl 2-formyl cyclopropane-1-carboxylic (1S,2S) acid.

So far as one knows, this compound is not described in the literature.

Stage B: Methyl ester of trans-3,3-dimethyl 2-formyl cyclopropane-1-carboxylic (1S,2S) acid, (III) with $R = -CH_3$ and trans (1S,2S) configuration.

The 75.9 g of oil containing the dimethyl-ketal of the methyl ester of the trans-3,3-dimethyl 2-formyl cyclopropane-1-carboxylic (1S,2S) acid are dissolved in 560 cc of an aqueous solution containing 30% of acetic acid, by warming to 80° C, under nitrogen. After fifteen minutes at 80° C, one cools, extracts with ether, washes the ethereal extracts with an aqueous solution of sodium bicarbonate, then with an aqueous solution of sodium chloride, dries them, concentrates them under vacuum and obtains, in the form of a yellow liquid, 53.5 g of the methyl ester of the trans-3,3-dimethyl 2-formyl cyclopropane-1-carboxylic (1S,2S) acid, b.pt. = 96° C under 14 mm of mercury; 2,4-dinitrophenyl-hydrazone, m.pt. = 172° C.

N.M.R. spectrum (deuterochloroform) It breaks down as follows: signals at 79 and 82 Mhz corresponding to the hydrogens of the methyls at 3; signal at 147.8 Mhz corresponding to the hydrogens at 1 and at 2 (doublet); signal at 224 Mhz corresponding to the hydrogens of the methyl in the ester function; signal at 573 Mhz corresponding to the hydrogen of the aldehyde function (doublet).

So far as one knows, this compound is not described in the literature.

Stage C: Lactone of cis-3,3-dimethyl 2-(methoxyhydroxymethyl) cyclopropane-1-carboxylic (1S,2R) acid or lactone of the methyl hemi-ketal of cis-3,3-dimethyl 2-formyl cyclopropane-1-carboxylic (1S,2R) acid. (IV) with $R'' = CH_3$ and cis (1S,2R) configuration.

Into 570 cc of methanol, one introduces under an atmosphere of nitrogen and in portions, 16.9 g of sodium, then when the sodium has been entirely utilised, 57.2 g of the methyl ester of trans-3,3-dimethyl 2-formyl cyclo-propane-1-carboxylic (1S,2S) acid, takes the reaction mixture to reflux, keeps it there for these hours, cools, eliminates the methanol by distillation under reduced pressure, acidifies with 200 cc of an aqueous 4 N solution of hydrochloric acid previously cooled to 0° C, extracts the aqueous phase with ethyl ether, washes the ethereal extracts with a saturated aqueous solution of sodium chloride, dries them, concentrates them to dryness under reduced pressure, and thus obtains 52.4 g of an oily residue containing the lactone of cis-3,3-dimethyl 2-(methoxyhydroxymethyl) cyclopropane-1-carboxylic (1S,2R) acid.

So far as one knows, this compound is not described in the literature.

Stage D: Lactone of cis-3,3-dimethyl 2-(dihydroxymethyl) cyclopropane-1-carboxylic (1S,2R) acid or internal hemi-acylal of cis-3,3, -dimethyl 2-formyl cyclopropane-1-carboxylic (1S,2R) acid, (V) of cis (1S,2R) configuration.

The 52.4 g of oily residue containing the lactone of cis-3,3-dimethyl 2-(methoxyhydroxymethyl) cyclopropane-1-carboxylic (1S,2R) acid, obtained in Stage C of Example I, are treated with 260 cc of water and 130 cc of dioxan. One carries the mixture to reflux for two hours, cools, concentrates to dryness by distillation under reduced pressure, dissolves the residue in a mixture of ether and methylene chloride, dries the solution, treats it with carbon black, and concentrates to dryness by distillation under reduced pressure. The residue is crystallized in isopropyl ether and one obtains 25 g of the lactone of cis-3,3-dimethyl 2-(dihydroxymethyl) cyclopropane-1-carboxylic (1R,2R) acid, m.pt. = 116° C.

A sample of this product is recrystallized in isopropyl ether, m.pt. = 116° C, $[\alpha]_D^{20}$ = +103° C ($c$ = 0.9%, ethanol).

Analysis: $C_7H_{10}O_3$ (142.15) Calculated: C% 59.14 H% 7.09 Found: 59.3 7.3

So far as one knows, this compound is not described in the literature.

Stage E: Cis-3,3-dimethyl 2-(2'-methoxycarbonyl-trans-1'-propenyl) cyclopropane-1-carboxylic (1S,2R) acid or 1-cis seq. trans-pyrethric (1S,2R) acid or 1-cis seq. trans-pyrethric (1S, 2R) acid a. Reaction:

Into 36 cc of tetrahydrofuran one introduces, under an atmosphere of nitrogen, 3 g of sodium amide (titrating 92%), then at 0° C a solution of 16.2 g of 0,0-diethyl 1-methoxycarbonyl ethylphosphonate, a compound prepared by applying the method of H.W.COOVER et al. Am. Soc. 79 1963 (1957), in 24 cc of tetrahydrofuran. One agitates the reaction mixture at 75° C for 2 hours, adds to it 1.8 g of sodium amide, then a solution of 6 g of the lactone of cis-3,3-dimethyl 2-(dihydroxymethyl) cyclopropane-1-carboxylic (1S,2R) acid in 42 cc of tetrahydrofuran, and agitates for two hours at +5° C. One pours the reaction mixture into a mixture of ice and 100 cc of an aqueous 2N solution of hydrochloric acid. By extraction with ether and elimination of the solvent, one obtains 8.06 g of crude product.

b. Preparation of the dextrorotatory alpha-phenylethylamine salt of cis sec. trans-pyrethric (1S,2R) acid:

This crude product is introduced in 14.3 cc of ethanol containing 10% of water, one warms to 60° C, adds 6.9 g of dextrorotatory alpha-phenylethylamine to the solution, allows it to crystallize slowly, isolates the precipitate formed by suction filtering, dries and obtains 10.2 g of the dextrorotatory alpha-phenylethylamine salt of cis-3,3-dimethyl 2-(2'-methoxycarbonyl-trans-1'-propenyl) cyclopropane-1-carboxylic (1S,2R) acid, m.pt. = 142° C, $[\alpha]_D^{20}$ = +22°.

So far as one knows, the (d) alpha-phenylethylamine salt of the cis seq. trans-pyrethric (1S,2R) acid is not known in the literature. c. Hydrolysis of the alpha-phenylethylamine salt:

One dissolves 10.2 g of the dextrorotatory alpha-phenylethylamine salt of the cis-3,3-dimethyl 2-(2'-methoxycarbonyl-trans-1'-propenyl) cyclopropane-1-carboxylic (1S,2R) acid at ambient temperature in a mixture of 51 cc of an aqueous 2 N solution of hydrochloric acid and 10 cc of ethyl ether, extracts the solution with ether, washes the ethereal extracts with water, dries them, eliminates the solvent and obtains 5.85 g of 1-cis-3,3-dimethyl 2-(2'-methoxycarbonyl-trans-1'-propenyl) cyclopropane-1-carboxylic (1S,2R) acid,- $[\alpha]_D^{20}$ = −12.5° ($c$ = 1%, carbon tetrachloride).

A sample of the product has been purified by two crystallizations of the dextrorotatory alpha-phenylethylamine salt, followed by acid hydrolysis, m.pt. = 76° C, $[\alpha]_D^{20}$ = −12.5° ($c$ = 1%, carbon tetrachloride).

Analysis: $C_{11}H_{16}O_4$ (212.24) Calculated: C% 62.25 H% 7.60 Found: 62.5 7.5

N.M.R. Spectrum (deuterochloroform)

The N.M.R. spectrum is in agreement with the "cis" configurations of the ring and the "trans" configuration of the olefinic chain. It breaks down as follows:
signals at 77 and 80.5 Mhz corresponding to the hydrogens of the methyls at 3;
signals at 115 and 116.5 Mhz corresponding to the hydrogens of the methyl in the lateral chain;
signal at 226 Mnz corresponding to the hydrogens of the methyl of the ester function;
signals at 418.5 and 426 Mhz corresponding to the hydrogen of the double bond in the lateral chain (doublet); signal at 634 Mhz corresponding to the hydrogen of the carbonyl at 1.

So far as one knows, the 1-cis-3,3-dimethyl 2-(2'-methoxycarbonyl-trans-1'-propenyl) cyclopropane-1-carboxylic (1S,2R) acid or 1-cis seq. trans-pyrethric (1S,2R) acid is not described in the literature.

EXAMPLE II:

Cis-3,3-dimethyl 2-(2'-methyl-1'-propenyl) cyclopropane-1-(Sheet I) carboxylic (1S,2R) acid or 1-cis-chrysanthemic (1S,2R) acid, ($I_A$) of cis (1S,2R) configuration or (I) with $R_1$ = Z = -CH$_3$ and cis (1S,2R) configuration.

a. Reaction:

One introduces 15.6 g of a suspension of 40% of sodium hydride in vaseline oil and 45 g of triphenyl-isopropyl phosphonium iodide into 200 cc of dimethoxyethane. One carries the reaction mixture to reflux, maintains it there for four hours, cools it, adds to it 10 g of the lactone of cis-3,3-dimethyl 2-(dihydroxymethyl) cyclopropane-1-carboxylic (1S,2R) acid, carries it back once more to reflux, maintains the reflux for one hour, cools, eliminates the solvent by distillation under reduced pressure, adds ethanol to destroy the excess of sodium hydride, adds water and ice, agitates, extracts the aqueous phase with methylene chloride, washes the methylene chloride extracts with a saturated aqueous solution of sodium chloride, eliminates the methylene chloride extracts, combines the principle aqueous phase with the aqueous washings, acidifies the aqueous solution thus obtained, extracts it with methylene chloride, washes the methylene chloride extracts with water, dries them and concentrates them to dryness.

The triphenyl-isopropyl phosphonium iodide can be prepared by application of the method of GEORG WITTIG DIETMAR WITTENBERG Annalen 606 1 (1957).

b. Separation of the 1-trans-chrysanthemic (1S,2S) acid:

The residual oil (9.9 g) is dissolved in the hot in a solution of 14.3 g of L (+) threo 1-p-nitrophenyl 2-dimethylaminopropane 1,3-diol in 27.5 cc of methanol. One adds 11 cc of isopropyl ether, cools slowly down to +5° C, allows to crystallize, suction filters the precipitate formed, dries it and obtains 14.16 g of the crude l-trans-chrysanthemic (1S,2S) acid salt. The mother liquors, a mixture of methanol and isopropyl ether, are set aside for recovery of the l-cis-chrysanthemic acid (Mother liquors A).

The crude salt is crystallized in a mixture of isopropyl ether and methanol (2/1) and one obtains 10.2 g of the L (+) threo 1-p-nitrophenyl 2-dimethylaminopropane 1,3-diol salt of l-trans-chrysanthemic (1S,2S) acid. This salt is introduced into an aqueous 2 N solution of hydrochloric acid. One agitates the mixture for half an hour at ambient temperature, extracts the aqueous phase with ethyl ether, washes the ethereal extracts with a saturated aqueous solution of sodium chloride, dries them, concentrates them to dryness under reduced pressure and obtains l-trans-chrysanthemic (1S,2S) acid, $[\alpha]_D^{20} = -18°$ ($c = 1\%$, ethanol).

c. Obtaining l-cis-chrysanthemic (1S,2R) acid:

The mother liquors A obtained above in paragraph b) of Example II, are concentrated to dryness under reduced pressure. The residue is introduced into an aqueous 2 N solution of hydrochloric acid. One agitates for half an hour at ambient temperature, extracts the aqueous phase with methylene chloride, washes the methylene chloride extracts with water, dries them, concentrates them to dryness and obtains 4.20 g of crude l-cis-chrysanthemic (1S,2R) acid (B). This crude acid can be purified in two ways:

1. Purification of l-cis chrysanthemic (1S,2R) acid by the (1)-quinine salt:

One employs 1.054 g of crude l-cis-chrysanthemic acid (B), which one dissolves in the hot in a solution of 2 g of laevorotatory quinine base in 4 cc of ethanol. One adds 1 cc of water and 3 cc of isopropyl ether, then slowly cools down to 5° C. One allows the crystallization to go to completion, suction filters, dries and obtains 2.06 g of the l-quinine salt of 3,3-dimethyl 2-(2′-methyl-1′-propenyl) cyclopropane-1-carboxylic (1S,2R) acid, m.pt. =110° C. By concentration of the mother liquors, one obtains a 2nd yield of 0.152 g of the equinine salt, m.pt. = 110° C.

The 1st and the 2nd yields of the quinine salt, obtained above, are reunited and introduced into an aqueous 2 N solution of hydrochloric acid. One agitates for half an hour at ambient temperature, extracts the aqueous phase with ether, washes the ethereal extracts with water, dries them, concentrates them to dryness and obtains 0.66 g of 3,3-dimethyl 2-(2′-methyl-1′-propenyl) cyclopropane-1-carboxylic (1S,2R) acid or l-cis-chrysanthemic (1S,2R) acid, m.pt. = 40° C, $[\alpha]_D^{20} = -36°$ ($c = 1\%$, ethanol).

2. Purification of l-cis-chrysanthemic (1S,2R) acid by the (d) alpha-phenyl-ethylamine salt:

One employs 2.085 g of crude l-cis-chrysanthemic (1S,2R) acid (B), which one dissolves in the hot in a solution of 1.5 g of dextrorotatory alpha-phenylethylamine in 10 cc of ethanol. One cools slowly to +5° C, allows the crystallization to go to completion, suction filters, dries and obtains 1.935 g of the alpha-phenylethylamine salt of 3,3-dimethyl 2-(2′-methyl-1′-propenyl) cyclopropane-carboxylic (1S,2R) acid, m.pt. = 130° C. By concentration of the mother liquors, one gets a 2nd yield of 0.265 g, m.pt. = 130° C.

These two yields of the alpha-phenylethylamine salt are reunited and introduced into an aqueous 2 N solution of hydrochloric acid. One agitates for half an hour at ambient temperature, extracts the aqueous phase with ethyl ether, washers the ethereal extracts with a saturated aqueous solution of sodium chloride, dries them, concentrates them to dryness under reduced pressure and obtains 1.21 g of 3,3-dimethyl 2-(2′-methyl-1′-propenyl) cyclopropane-1-carboxylic (1S,2R) acid or l-cis-chrysanthemic (1S,2R) acid, m.pt. = 40° C, $[\alpha]_D^{20} = -39°$ ($c = 1\%$, ethanol).

The l-quinine salt of l-cis-chrysanthemic (1S,2R) acid, the (+) alpha-phenylethylamine salt of l-cis-chrysanthemic (1S,2R) acid and the l-cis-chrysanthemic (1S,2R) acid are identical to compounds obtained by I.G.M. CAMPBELL and S.H. HARPER J. Sci. Food. Agr. 3, 189 (1952).

Example III:

Cis-3,3-dimethyl 2-(2′-methoxycarbonyl-trans-1′-propenyl) (Sheet I) cyclopropane-1-carboxylic (1R,2S) acid or d-cis seq. trans-pyrethric (1R,2S) acid ($I_B$) of cis (1R,2S) configuration or (I) with $R_1$ =—$CH_3$, Z =—$CO_2CH_3$ and cis (1R,2S) configuration.

Stage A: Dimethyl-ketal of the methyl ester of trans-3,3-dimethyl 2-formyl cyclopropane-1-carboxylic (1R,2R) acid (II′) of trans (1R,2R) configuration with R =—$CH_3$ and alkyl =—$CH_3$.

In an analogous manner to that of Stage A of Example I, starting from 106 g of the methyl ester of d-trans-chrysanthemic (1R,2R) acid, one obtains 116 g of oil containing the dimethyl-ketal of the methyl ester of the trans-3,3-dimethyl-2-formyl cyclopropane-1-carboxylic (1R,2R) acid.

So far as one knows, this compound is not described in the literature.

Stage B: Methyl ester of trans-3,3-dimethyl 2-formyl cyclopropane-1-carboxylic (1R,2R) acid (III) of trans (1R,2R) configuration with R =—$CH_3$.

In an analogous manner to that of Stage B of Example I, starting from 116 g of oil containing the dimethyl-ketal of the methyl ester of trans-3,3-dimethyl 2-formyl cyclopropane-1-carboxylic (1R,2R) acid, one obtains 85 g of the methyl ester of trans-3,3-dimethyl 2-formyl cyclopropane-1-carboxylic (1R,2R) acid.

So far as one knows, this compound is not described in the literature.

Stage C: The lactone of cis-3,3-dimethyl 2-(methoxyhydroxymethyl) cyclopropane-1-carboxylic (1R,2S) acid or the lactone of the methyl hemiketal of cis-3,3-dimethyl 2-formyl cyclopropane-1-carboxylic (1R,2S) acid (IV, with R″ =—$CH_3$ and cis (1R,2S) configuration).

In an analogous manner to that of Stage C of Example I, one obtains starting from 127 g of the methyl ester of trans-3,3-dimethyl-2-formyl cyclopropane-1-carboxylic (1R,2R) acid, 100 g of an oily residue containing the lactone of cis-3,3-dimethyl 2-(methoxyhydroxymethyl) cyclopropane-1-carboxylic (1R,2S) acid.

So far as one knows, this compound is not described in the literature.

Stage D: The lactone of cis-3,3-dimethyl 2-(dihydroxymethyl)/cyclopropane-1-carboxylic (1R,2S) acid or internal hemi-acylal of cis-3,3-dimethyl 2formyl cyclopropane-1-carboxylic (1R,2S) acid (V, of cis (1R,2S) configuration).

In a manner analogous to that of Stage D of Example I, one obtains, starting from 100 g of the oily residue containing the lactone of cis-3,3-dimethyl 2-(methoxyhydroxymethyl) cyclopropane-1-carboxylic (1R,2S) acid, 57.7 g of the lactone of cis-3,3-dimethyl 2(dihydroxymethyl) cyclopropane-1-carboxylic (1R,2S) acid, m.pt. = 116° C.

A sample of this product is crystallized in isopropyl ether, m.pt. = 116° C, $[\alpha]_D^{20} = -102°$ ($c = 1.1\%$, ethanol).

Analysis: $C_7H_{10}O_3$ (142.15)
Calculated: C% 59.14 H% 7.09
Found: 58.8 7.2

So far as one knows, this compound is not described in the literature.

Stage E: Cis-3,3-dimethyl-2(2'-methoxycarbonyl-trans-1'-propentyl) cyclopropane-1-carboxylic (1R,2S) acid or d-cis seq. trans-pyrethric (1R,2S) acid.

One introduces 10 g of sodium amide (titrating 95%) into 120 cc. of tetrahydrofuran under an atmosphere of nitrogen, followed at −5° C by a solution of 46 g of 0,0-dimethyl 1-methoxycarbonylethyl phosphonate in 80 cc of tetrahydrofuran. One agitates the reaction mixture at ambient temperature for three hours and thirty minutes, adds to it 5 g of sodium amide, then a solution of 20 g of the lactone of cis-3,3-dimethyl 2-(dihydroxymethyl) cyclopropane-1-carboxylic (1R,2S) acid in 120 cc of tetrahydrofuran, and agitates for three hours at ambient temperature. One concentrates the reaction mixture to dryness by distillation under reduced pressure. One adds to the residue a mixture of water and ice, extracts the aqueous phase with ethyl ether, eliminates these ethereal extracts, acidifies the aqueous phase, saturates it with sodium chloride, extracts it with ethyl ether, washes the reunited ethereal extracts with a saturated solution of sodium chloride, dries them and concentrates them to dryness.

The residue is introduced into a mixture of 170 cc of ethanol, 17 cc of acetic acid and 17 g of Reagent T or trimethylamino aceto hydrazide hydrochloride. The mixture is carried to reflux, one maintains it there for one hour, then pours it onto a mixture of water, ice and 25.5 cc of an aqueous 10 N solution of soda. One extracts the aqueous phase with ethyl ether, washes these reunited ethereal extracts with a saturated solution of sodium chloride, dries them and concentrates them to dryness under reduces pressure.

The product obtained, freed from its carbonylated impurities, is redistilled under reduced pressure and one obtains 7.3 g of 3,3-dimethyl 2-(2'-methoxycarbonyl-trans-1'-propenyl) cyclopropane-1-carboxylic (1R,2S) acid or d-cis seq. trans-pyrethric (1R,2S) acid, b.pt. = 150° C under 0.3 mm of mercury, m.pt. = 70° C (not very well defined),$[\alpha]_D^{20} = +11.5°$, ($c = 1.2\%$, carbon tetrachloride).

A further redistillation of the fractions disgarded during the first redistillation makes it possible to obtain a second yield of identical quality to the first yield obtained above.

Analysis: $C_{11}H_{16}O_4$ (212.24)
Calculated: C% 62.25 H% 7.60
Found: 62.1 7.6 N.M.R. Spectrum (deuterochloroform)

The N.M.R. spectrum is in agreement with the "cis" configuration of the ring and the "trans" configuration of the olefinic chain. It breaks down as follows:- signals at 77.5 and 80.5 Mhz corresponding to the hydrogens of methyls at 3; signals at 116 and 117.5 Mhz corresponding to the hydrogens of the methyl in the side chain; signal at 226 Mhz corresponding to the hydrogens of the methyl of the ester function; signals at 421 and 428 Mhz corresponding to the hydrogen of the double bond of the side chain (doublet); signal at 673 Mhz corresponding to the hydrogen of the carboxyl at 1.

So far as one knows, this compound is not described in the literature.

EXAMPLE IV:

Cis-3,3-dimethyl 2-(2'-methyl-1'-propenyl) cyclopropane-1-carboxylic acid or d-cis-chrysanthemic (1R,2S) acid ($I_4$), of cis (1R,2S) configuration or (I) with $Z = R_1 = -CH_3$ and cis (1R,2S) configuration.

a. Reaction:

One introduces 11.5 g of a suspension of 40% of sodium hydride in vaseline oil and 33.4 g of triphenylisopropyl phosphonium iodide into 148 cc of dimethoxyethane. One carries the reaction mixture to reflux, maintains it there for four hours, cools it, adds to it 7.4 g of the lactone of cis-3,3-dimethyl 2-(dihydroxymethyl) cyclopropane-1-carboxylic (1R,2S) acid, carries it back once more to reflux, maintains reflux for one hour, cools, eliminates the solvent by distillation under reduced pressure, adds ethanol to destroy the excess of sodium hydride, adds water and ice, agitates, extracts the aqueous phase with methylene chloride, washes the methylene chloride extracts with a saturated aqueous solution of sodium chloride, eliminates the methylene chloride, combines the principle aqueous phase with the aqueous washings, acidifies the aqueous solution thus obtained, extracts it with methylene chloride, washes the methylene chloride extracts with water, dries them and concentrates them to dryness.

b. Separation and purification of the d-cis-chrysanthemic (1R,2S) acid:

The residue obtained is dissolved in 15 cc of aqueous ethanol containing 10% of water (solution A). One separately dissolves 15 g of laevorotatory quinine base in 30 cc of aqueous ethanol containing 10% of water (solution B). One heats solutions A and B up to 70° C and introduces solution B into solution A. One cools the mixture down to +5° C, allows it to crystallize, suction filters the precipitate formed, dries it, crystallizes it in aqueous ethanol containing 10% of water and obtains 10.95 g of the 1-quinine salt of d-cis-chrysanthemic (1R,2S) acid, m.pt. = 115°-120° C (not very well defined).

The 10.95g of quinine salt are introduced into 20 ccs of an aqueous 2 N solution of hydrochloric acid. One agitates for ten minutes, extracts the aqueous phase with methylene chloride, washes the methylene chloride extracts with a saturated aqueous solution of sodium chloride, dries them, concentrates them to dryness and obtains 3.45 g of 3,3-dimethyl 2(2'-methyl-1'-propenyl) cyclopropane-1-carboxylic (1R,2S) acid or d-cis-chrysanthemic (1R,2S) acid, m.pt. = about 40° C, $[\alpha]_D^{20} = +36.4°$ ($c = 1\%$, ethanol). A sample of this product has been purified by crystallisations of the quinine salt, followed by acid hydrolysis.

The product thus purified melts at 42° C and its rotatory power is $[\alpha]_D^{20} = +41°$ ($c = 1\%$, ethanol).

The I.R. and N.M.R. spectra of this product confirm the cis structure.

Circular Dichroism (dioxan)
Max. at 215 m$\mu$ $\Delta\epsilon = +14.6$
Min. at 253 m$\mu$ $\Delta\epsilon = -1.2$ The d-cis-chrysanthemique (1R,2S) acid thus obtained is identical to the compound described by I.G.M. CAMPBELL and S.H. HARPER J. Sci. Food 3, 189 (1952).

EXAMPLE V: (Sheet III)

Internal hemi-acylal of cis-3,3-dimethyl-2-formyl-cyclopropane-1-carboxylic (1S,2R) acid (V, of cis (1S,2R) configuration)

Stage A: Trans-3,3-dimethyl-2-formyl-cyclopropane-1-carboxylic (1S,2S) acid (IX, of trans (1S,2S) configuration)

One dissolves 20 g. of 1-trans-chrysanthemic (1S,2S) acid in 250 cc. of methanol, takes the temperature to −80° C and bubbles in a current of ozonised oxygen until the appearance of a blue coloration. Then one bubbles a current of oxygen for fifteen minutes into the reaction mixture, then a current of nitrogen during forty-five minutes. One slowly adds 10 cc . of dimethyl sulphide, maintains the reaction mixture at about −35° C for thirty minutes, then for one hour at 0° C and finally for one hour at ambient temperature. One eliminates the solvent by distillation under reduced pressure, introduces the residue into a solution of 17 g. of trimethylamino aceto hydrazide chloride (reagent T) in 170 cc. of ethanol and 17 cc. of acetic acid. One carries the reaction mixture to reflux, keeps it there for one hour, cools it, pours it into a dilute solution of soda, extracts it with ether to eliminate the non-aldehydic fraction, acidifies with a dilute aqueous solution of hydrochloric acid, extracts the aqueous acidic phase with ether, washes the ethereal solutions, dries them, concentrates them to dryness, pastes the residue with petroleum ether (b.pt. = 35° − 75° C) and obtains 5.80 g. trans-3,3-dimethyl-2-formyl-cyclopropane-1-carboxylic (1S,2S) acid In an analogous manner, starting from d-trans-chrysanthemic (1R,2R) acid or racemic trans-chrysanthemic acid, one prepares respectively trans-3,3-dimethyl-2-formyl-cyclopropane-1-carboxylic (1R,2R) acid or racemic trans-3,3-dimethyl-2-formyl-cyclopropane-1-carboxylic acid.

So far as one knows, the trans-3,3-dimethyl-2-formyl-cyclopropane-1-carboxylic (1S,2S) acid and the racemate are not described in the literature.

Stage B: Dimethyl-ketal of trans-3,3-dimethyl-2-formyl-cyclopropane-1-carboxylic (1S,2S) acid (X, with alkyl = —$CH_3$)

One introduces 13.8 g. of trans-3,3-dimethyl-2-formyl-cyclopropane-1-carboxylic (1S,2S) acid under an atmosphere of nitrogen into 100 cc of methanol, maintains the solution at reflux for twenty-four hours while recycling the distillate through a column packed with "siliporite" (dehydrated alkali metal aluminum silicates), concentrates to dryness, recovers the crystals impregnated with an oily impurity which one eliminates by suction filtering, takes up the crystals once more in petroleum ether (b.pt. = 65° - 75° C), suction filters, dries and obtains 11.7 g. of the dimethyl-ketal of trans-3,3-dimethyl-2-formyl-cyclopropane-1-carboxylic (1S,2S) acid, m.pt. = 65° C.

Analysis: $C_9H_{16}O_4$ (188.22)
Calculated: C% 57.43 H% 8.57
Found: 57.6 8.5

In an analogous manner, starting from trans-3,3-dimethyl-2-formyl-cyclopropane-1-carboxylic (1R,2R) acid or from racemic trans-3,3-dimethyl-2-cyclopropane-1-carboxylic acid, one obtains respectively the dimethyl-ketal of trans-3,3-dimethyl-2-formyl-cyclopropane-1-carboxylic (1R,2R) acid, m.pt. = 65° C, or the dimethyl-ketal of racemic trans-3,3-dimethyl-2-formyl-cyclopropane-1-carboxylic acid.

So far as one knows, the dimethyl-ketals of trans-3,3-dimethyl-2-formyl-cyclopropane-1-carboxylic (1S,2S), (1R,2R) acid or the racemate are not described in the literature.

Stage C: The Lactone of the methyl hemi-ketal of cis-3,3-dimethyl-2-formyl-cyclopropane-1-carboxylic (1S,2R) acid (IV, with alkyl = —$CH_3$ and cis (1S,2R) configuration)

One introduces 5 g. of the dimethyl-ketal of trans-3,3-dimethyl-2-formyl-cyclopropane-1-carboxylic (1S,2S) acid and 0.21 g. of para-toluene-sulphonic acid into 175 cc. of benzene under an atmosphere of nitrogen. One carries the reaction mixture to reflux and maintains it distilling while keeping the volume of the reaction mixture constant by continuous addition of benzene. At the end of six hours, one cools, eliminates the benzene by distillation, pours the reaction mixture into an aqueous solution of sodium bicarbonate containing ice, then by extractions with ether and concentration to dryness, obtains 1.9 g. of the lactone of the methyl hemi-ketal of cis-3,3-dimethyl-2-formyl-cyclopropane-1-carboxylic (1S,2R) acid, b.pt. = 60° C under 0.3 mm. of mercury. I.R. Spectrum (chloroform)

It confirms the absence of free hydroxyl and includes a band at $1,764^{cm-1}$ corresponding to the carbonyl of a gamma-lactone.

In an analogous manner, starting from the dimethyl-ketal of trans-3,3-dimethyl-2-formyl-cyclopropane-1-carboxylic (1R,2R) acid or the corresponding racemate, one obtains respectively the lactones of the methyl hemi-ketals of cis-3,3-dimethyl-2-formyl-cyclopropane-1-carboxylic (1R,2S) acid or the corresponding racemate.

Stage D: Internal hemi-acylal of cis-3,3-dimethyl-2-formyl-cyclopropane-1-carboxylic (1S,2R) acid (V, of cis (1S,2R) configuration)

One introduces the 1.9 g. of the lactone of the methyl hemi-ketal of the cis-3,3-dimethyl-2-formyl-cyclopropane-1-carboxylic (1S,2R) acid into a mixture of 25 cc . of water and 12.5 cc . of dioxan, maintains this for one hour at 60° C, concentrates to dryness under reduced pressure and obtains 0.55 g. of the internal kemi-acylal of cis-3,3-dimethyl-2-formyl-cyclopropane-1-carboxylic (1S,2R) acid, m.pt. = 114° C. A sample of this product is crystallised in isopropyl ether, m.pt. = 116° C, $[\alpha]_D^{20} = +103°$ (c = 1%, methanol).

In an analogous manner, starting from the lactones of the methyl-hemi-ketals of cis-3,3-dimethyl-2-formyl-cyclopropane-1-carboxylic (1R,2S) acid or the corresponding racemate, one obtains respectively the internal hemi-acylals of cis-3,3-dimethyl-2-formyl-cyclopropane-1-carboxylic (1R,2S) acid, m.pt. = 116° C $[\alpha]_D^{20} = -102°$ (c =1%, ethanol), or of the corresponding racemate.

EXAMPLE VI: (Sheet III)

Internal hemi-acylal of cis-3,3-dimethyl-2-formyl-cyclopropane-1-carboxylic (1S,2R) acid (V, of cis (1S,2R) configuration)

Stage A: Dimethyl-ketal of the methyl ester of trans-3,3-dimethyl-2-formyl-cyclopropane-1-carboxylic (1S,2S) acid (VIII, with alkyl = —$CH_3$ and (1S,2S) configuration)

Treatment with ozone:
One passes a current of ozone for about three and a half hours into a solution cooled to −80° C of 70 g. of the methyl ester of 1-trans-chrysanthemic (1S,2S) acid in 700 cc . of methanol, then drives off the excess ozone by a current of argon, while always maintaining the temperature at −80° C.

Reduction by dimethyl-thioether:

The methanolic solution obtained previously is adjusted to −40° C and one adds to it, while agitating, 79 cc . of dimethyl-thioether. One allows the temperature to rise to about 20° C and keeps the reaction mixture under agitation and nitrogen for some hours. One eliminates the methanol by distillation under reduced pressure, takes up once more in methylene chloride, washes with an aqueous solution of sodium bicarbonate then with water, dries, and concentrates to dryness under reduced pressure.

One thus obtains 75.9 g. of oil which contains the methyl ester of the dimethyl-ketal of trans-3,3-dimethyl-2-formyl-cyclopropane-1-carboxylic (1S,2S) acid.

In an analogous manner, starting from the methyl esters of trans-chrysanthemic (1R,2R) acid or the corresponding racemate, one obtains respectively the methyl esters of the dimethyl-ketals of trans-3,3-dimethyl-2-formyl-cyclopropane 1-carboxylic (1R,2R) acid or the corresponding racemate.

Stage B: Methyl ester of trans-3,3-dimethyl-2-formyl-cyclopropane-1-carboxylic (1S,2S) acid (VIII′, with R = —CH₃ and trans (1S,2S) configuration).

The 75.9 g. of oil containing the methyl ester of the dimethyl ketal of the trans-3,3-dimethyl-2-formyl-cyclopropane-1-carboxylic (1S,2S) acid are dissolved in 560 cc . of an aqueous solution containing 30% of acetic acid, by warming to 80° C under nitrogen. After fifteen minutes at 80° C, one cools, extracts with ether, washes the ethereal extracts with anaqueous solution of sodium bicarbonate then with an aqueous solution of sodium chloride, dries them, concentrates them under vacuum and obtains, in the form of a yellow liquid, 53.5 g. of methyl ester of trans-3,3-dimethyl-2-formyl-cyclopropane-1-carboxylic (1S,2S) acid, b.pt. = 96° C under 14 mm. of mercury; 2,4-dinitrophenylhydrazone m.pt. = 172° C.

N.M.R Spectrum (deuterochloroform)

It breaks down as follows:- signals at 79 and 82 Mhz corresponding to the hydrogens of the methyls at 3; signal at 147.8 Mhz corresponding to the hydrogens at 1 and at 2 (doublet); signal at 224 Mhz corresponding to the hydrogens of the methyl of the ester function; signal at 573 Mhz corresponding to the hydrogen of the aldehyde function (doublet).

In an analogous manner, starting from the methyl esters of the dialkyl-ketal of trans-3,3-dimethyl-2-formyl-cyclopropane-1-carboxylic (1R,2R) acid or the corresponding racemates, one obtains respectively the methyl esters of trans-3,3-dimethyl-2-formyl-cyclopropane-1-carboxylic (1R,2R) acid or the corresponding racemate.

Stage C: Trans-3,3-dimethyl-2-formyl-cyclopropane-1-carboxylic (1S,2S) acid ( I X , of trans (1S,2S) configuration)

One introduces 15.6 g. of the methyl ester of trans-3,3-dimethyl-2-formyl-cyclopropane-1-carboxylic (1S,2S) acid into a mixture of 100 cc . of methanol, 11.cc of an aqueous 10N solution of soda and 20 cc . of water under an inert atmosphere, carries this reaction mixture of reflux and maintains it there for 1 hour. After evaporation of the solvent under reduced pressure, one dilutes with water, extracts with ether what has not been saponified, acidifies the aqueous phase with a concentrated aqueous solution of hydrochloric acid, extracts the liberated acid with ether, washes the ethereal solutions, dries them, concentrates them to dryness and obtains 12 g. of trans-3,3-dimethyl-2-formyl-cyclopropane-1-carboxylic (1S,2S) acid.

In an analogous manner, starting from the methyl esters of trans-3,3-dimethyl-2-formyl-cyclopropane-1-carboxylic (1R,2R) acid or the corresponding racemate, one obtains respectively the trans-3,3-dimethyl-2-formyl-cyclopropane-1-carboxylic (1R,2R) acid or the corresponding racemate.

These compounds are identical to those obtained in Stage A of Example V.

One then finally undertakes the preparation of the internal hemi-acylal of the cis-3,3-dimethyl-2-formyl-cyclopropane-1-carboxylic (1S,2R) acid according to stages B, C and D of Example V.

We claim:

1. A process for the preparation of racemic or optically active cyclopropane carboxylic acids of the formula

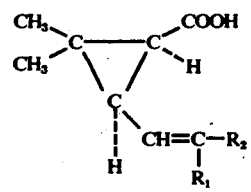

wherein the COOH on the 1-carbon and the

on the two carbon are cis relative to each other and $R_1$ and $R_2$ are selected from the group consisting of ethyl and methyl or $R_1$ is methyl and $R_2$ is methoxy carbonyl or $R_1$ and $R_2$ together with the carbon atom to which they are attached form a cyclopentyl comprising submitting the internal hemiacylal of racemic or optically active cis 3,3-dimethyl-2-formyl-cyclopropane-1-carboxylic acid of the formula

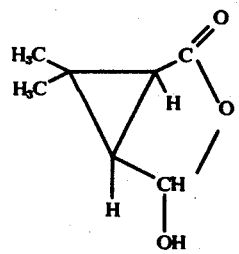

in the presence of an organic solvent to the action of a phosphorus reagent selected from the group consisting of an ylide of the formula

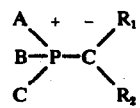

in the presence of an alkali metal hydride and a carbanion of the formula

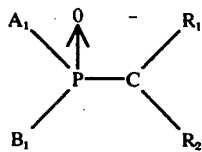

wherein A, B, and C are selected from the group consisting of phenyl, dialkylamino and dialkylamino diaryl, $A_1$ and $B_1$ are selected from the group consisting of phenyl, dialkylamino and alkoxy and $R_1$ and $R_2$ have the above meaning in the presence of an alkali metal amide or alkali metal alcoholate to form the corresponding racemic or optically active cyclopropane carboxylic acid.

2. A process for the preparation of racemic or optically active cyclopropane carboxylic acids of the formula

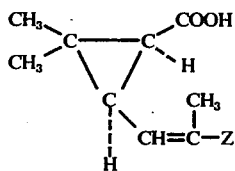

wherein the COOH on the 1-carbon atom and the

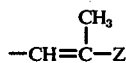

on the 2-carbon atom are cis relative to each other and Z is selected from the group consisting of methyl and methoxycarbonyl which comprises reacting the internal hemiacylal of racemic or optically active cis 3,3-dimethyl-2-formyl-cyclopropane-1-carboxylic acid of the formula

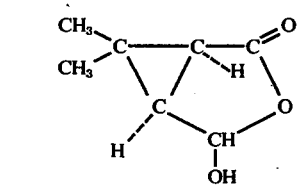

in the presence of an organic solvent with a phosphorus reagent selected from the group consisting of an ylide of the formula

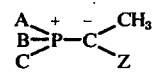

in the presence of an alkali metal hydride and a carbanion of the formula

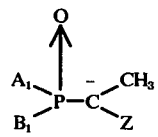

wherein Z has the above definition and A, B, and C are selected from the group consisting of phenyl, dialkylamino and dialkylamino diaryl, $A_1$ and $B_1$ are selected from the group consisting of phenyl, dialkylamino and alkoxy in the presence of an alkali metal amide or alkali metal alcoholate to form the corresponding racemic or optically active cyclopropane carboxylic acid.

3. The process of claim 1, which comprises reacting an o,o-dialkyl 1-methoxy-carbonyl ethyl phosphonate such as o,o-diethyl 1-methoxycarbonyl ethyl phosphonate in the presence of tetrahydrofuran with the internal hemi-acylal of cis-3,3-dimethyl-2-formyl-cyclopropane-1-carboxylic (1S,2R) acid in a basic medium, to form 1cis seq.trans-pyrethric (1S,2R) acid.

4. The process of claim 1, which comprises reacting a triarylisopropyl phosphonium salt such as triphenylisopropyl phosphonium iodide in the presence of dimethoxyethane with the internal hemi-acylal of cis-3,3-dimethyl-2-formyl-cyclopropane-1-carboxylic (1S,2R) acid in a basic medium, to form 1-cis-chrysanthemic (1S,2R) acid.

* * * * *